United States Patent [19]

Lazarevski et al.

[11] Patent Number: 5,268,462
[45] Date of Patent: Dec. 7, 1993

[54] OLEANDOMYCIN OXIMES

[75] Inventors: Gorjana Lazarevski; Slobodan Djokic, both of Zagreb, Yugoslavia

[73] Assignee: Pliva Farmaceutska, Zagreb, Yugoslavia

[21] Appl. No.: 669,728

[22] Filed: Mar. 14, 1991

[30] Foreign Application Priority Data

Mar. 21, 1990 [YU] Yugoslavia ............... 556/90

[51] Int. Cl.$^5$ ............................... C07H 17/08
[52] U.S. Cl. ................................... 536/7.4
[58] Field of Search ............ 536/7.2, 7.4; 514/29

[56] References Cited

U.S. PATENT DOCUMENTS 4,063,014  12/1977  Hallas et al. .................. 536/7.3
4,069,379   1/1978  Schiavolino .................. 536/7.2
4,180,654  12/1979  Schiavolino .................. 536/7.3

OTHER PUBLICATIONS

Hochstein et al., Journal of American Chemical Society, vol. 82, pp. 3225-3227.

Primary Examiner—Johnnie R. Brown
Assistant Examiner—Elli Peselev
Attorney, Agent, or Firm—Pollock, Vande Sande & Priddy

[57] ABSTRACT

Oleandomycin oximes

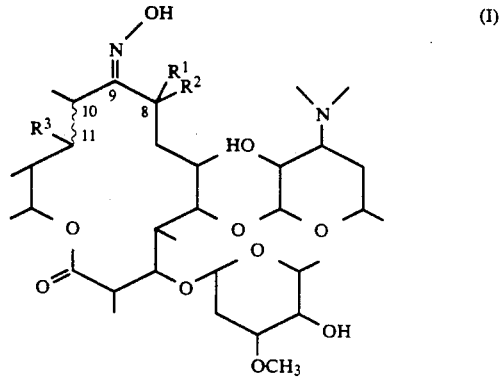

wherein $R^1$ stands for hydrogen or —$CH_3$, $R^2$ stands for —$CH_3$ or hydrogen or $R^1$ and $R^2$ stand together for an epoxide group or for =$CH_2$, $R^3$ stands for —OH, whereas the ∼ line stands for a single or a double bond, a process for the preparation thereof and their use in antimicrobial agents.

5 Claims, No Drawings

OLEANDOMYCIN OXIMES

The present invention relates to oleandomycin oximes, to a process for the preparation of oleandomycin oximes and to their use in antimicrobial agents.

Oleandomycin is a 14-membered macrolide antibiotic possessing an activity spectrum similar to that of erythromycin. It was described for the first time in U.S. Pat. No. 2,757,123. The structural representation of oleandomycin shows a 14-membered lactone ring, comprising a keto group in C-9 position and bearing two sugar moieties (desosamine in C-5 position; and oleandrose in C-3 position) and three —OH groups (cf. formula IIa, hereinafter).

It differs from other polyoxo macrolides by the presence of an exocyclic epoxide ring on the C-8 atom. Hitherto, there have been described numerous chemical transformations of the above-mentioned functional groups. It has been known that the dehydration of the —OH group in position C-11 under slightly alkaline conditions results in a double bond between the C-10 and C-11 atoms of the aglycone ring, upon formation of the anhydro oleandomycin (J. Am. Chem. Soc., 82, 3225, 1960) (cf. formula IIb, represented hereinafter).

It has been known as well (U.S. Pat. No. 4,069,379) that the epoxide group may be converted into the methylene group by conducting the reaction with $CrCl_2$ in reaction-inert solvents, yielding a compound of formula IIc (represented hereinafter).

Furtheron, it has been known that the catalytical reduction of the exocyclic methylene group in position C-8 yields a mixture of 8-methyl-oleandomycin anomers of formulae IId and IIe (W. D. Celmer, Pure Appl. Chem., 28, 413, 1971).

The currently most suitable technical and preparative method of preparing oximes has been the reacting of aldehydes and ketones with an excess of hydroxylamine hydrochloride in the presence of inorganic or organic bases, e.g. $BaCO_3$, $NaHCO_3$, triethylamine and pyridine, in a solvent chosen from alcohols or an excess of an organic base (Methoden der Org. Chem., 4$^{th}$ Ed., Vol. X/4, p. 55).

Conventional oximation reactions are not applicable to oleandomycin in virtue of the known sensitivity of the oleandomycin molecule. The performance of the reaction in acidic medium and at elevated temperatures results in the breaking up of the epoxide, the elimination of the sugar moieties, and the trans-lactonization, whereas an alkaline medium causes dehydration. On the other hand, somewhat severe oximation conditions, e.g. increased temperature, in some cases increased pressure, strong bases, prolonged reaction times are indicated owing to the steric hindrance of the C-9 keto group (J. Org. Chem., 28, 1557, 1963).

There was a need to provide oleandomycin oximes and a process which would fulfill all the aforesaid rather contradictory requests and ensure the performance of the reaction in the desired position, leaving the remaining part of the molecule unaltered.

The present invention provides oleandomycin oximes of formula I

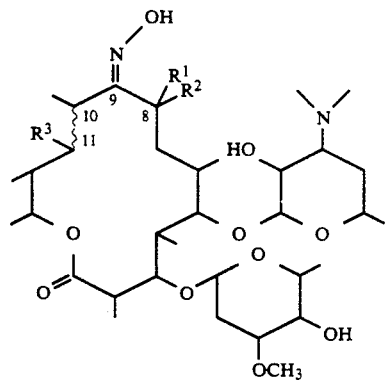

wherein $R^1$ stands for hydrogen or —$CH_3$, $R^2$ stands for —$CH_3$ or hydrogen or $R^1$ and $R^2$ stand together for an epoxide group or for =$CH_2$, $R^3$ stands for —OH, whereas the line ～ stands for a single or a double bond.

Particular compounds of formula (I) are compounds Ia–Ie:

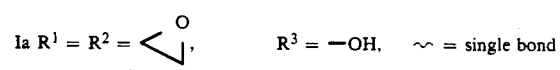

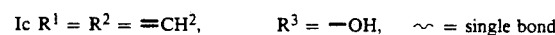

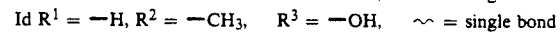

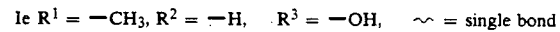

Oleandomycin oximes of formula (I) are deemed to be novel.

As a further feature of the present invention there is provided a process for the preparation of oleandomycin oximes (I), comprising the reaction of oleandomycin of formula (II)

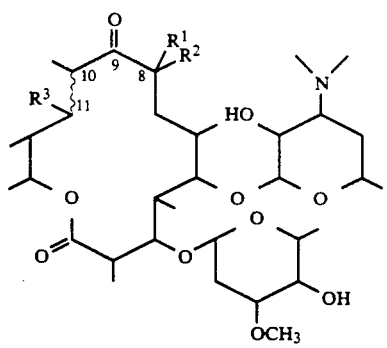

wherein $R^1$, $R^2$, $R^3$ and the line ～ have the hereinabove mentioned meanings, with an excess of hydroxylamine hydrochloride.

In particular, the compounds (Ia)–(Ie) as cited hereinabove can be obtained by reacting compounds (IIa)–(IIe):

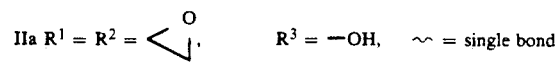

IIb $R^1 = R^2 = $ 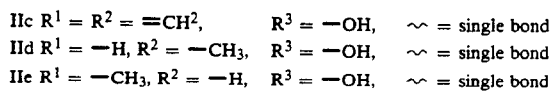, $\sim$ = double bond

| | | | |
|---|---|---|---|
| IIc $R^1 = R^2 = =CH_2$, | $R^3 = -OH$, | $\sim$ = single bond |
| IId $R^1 = -H, R^2 = -CH_3$, | $R^3 = -OH$, | $\sim$ = single bond |
| IIe $R^1 = -CH_3, R^2 = -H$, | $R^3 = -OH$, | $\sim$ = single bond | with an excess of hydroxylamine hydrochloride.

Said reaction can be carried out with a 4–6 molar excess of hydroxylamine hydrochloride, in the presence of an excess of pyridine serving additionally as a solvent, in a nitrogen stream, at ambient temperature, within of 2–40 hours.

The completion of the reaction was determined by thin layer chromatography (TLC) on silicagel plates 60 $F_{254}$ in the following systems:
A) $CHCl_3/CH_3OH$/conc. $NH_4OH$(6:1:0.1)
B) $CH_2Cl_2/CH_3OH$/conc. $NH_4OH$(90:9:1.5)

The isolation of the products was performed by extraction with halogenated solvents, e.g. chloroform or methylene chloride, within a pH range of 7.0–8.5, and finally by evaporation of the organic extract to dryness.

The preparation of 8-methyl-oleandomycin oximes of formulae (Id) and (Ie) started from a mixture of 8-methyl-oleandomycin anomers of formulae (IId) and (IIe), which was without prior separation directly subjected to the oximation reaction. There was obtained a crude product, comprising a mixture of anomer oximes of formulae (Id) and (Ie), which was separated by chromatography on a silica gel column; elution with a mixture of $CH_2Cl_2/CH_3OH$ (85:15).

The antibacterial in vitro activity was evidenced on a series of standard and clinically isolated strains. The results are expressed as Minimal Inhibitory Concentration (MIC; μg/mL) and represented hereinbelow in Tables 1 and 2.

TABLE 1

Antibacterial in vitro activity of 8-methyl-oleandomycin oxime (Ie) in comparison with oleandomycin phosphate against standard strains

| Test Organism | Minimal Inhibitory Concentrations (MIC in μg/mL) | |
|---|---|---|
| | oleandomycin phosphate | Ie |
| Staph. aureus ATCC 6538-P | 0.4 | 0.2 |
| Strept. faecalis ATCC-8043 | 0.8 | 0.2 |
| Sarcina lutea ATCC-9341 | 0.2 | 0.2 |
| E. coli ATCC 10536 | 25 | 6.2 |
| Klebsiella pneum. NCTC-10499 | >50 | 50 |
| Pseud. aerug. NCTC-10490 | >50 | 50 |

TABLE 2

Antibacterial in vitro activity of 8-methyl-oleandomycin oxime (Ie) in comparison with oleandomycin phosphate against clinical isolates

| Test Organism | Minimal Inhibitory Concentrations (MIC in μg/mL) | |
|---|---|---|
| | oleandomycin phosphate | Ie |
| Staph. aureus 10099 | 0.8 | 0.4 |
| Staph. saprophyt. 3947 | 1.6 | 1.6 |
| Strept. faecalis | 3.1 | 0.8 |
| Staph. aureus 10097 | 0.8 | 0.4 |
| Strept. pneumoniae 4050 | 1.6 | 0.4 |
| H. Influenze 4028 | — | 0.4 |

The invention is illustrated by the following Examples.

EXAMPLE 1

OLEANDOMYCIN OXIME Ia

To a solution of oleandomycin phosphate (IIa) (13.4 g, 0.00186 mole) in 19 mL of dry pyridine there was added $NH_2OH.HCl$ (6 g, 0.086 mole) and the reaction mixture was stirred at room temperature in nitrogen stream for 2 hours. Water (400 ml) was added to the reaction mixture and it was extracted with dichloromethane by means of gradient extraction at pH 5 and 7. The organic extract was evaporated at pH 7.0 and at reduced pressure to dryness and the residue was dried in high vacuum at 40° C., yielding 9.1 g (70.0%) of the product.

$R_f$
(A) 0.51
(B) 0.32
M+ 702
UV (MeOH): the peak at 290 nm disappears

$^1$H-NMR (DMSO-$d_6$) δ, ppm: 2.23 [6H, s, $(CH_3)_2N-$], 3.33 (3H, s, 3''—$OCH_3$), 10.82 (=NOH), disappears by exchange with $D_2O$ $^{13}$C-NMR (CDCl$_3$) δ, ppm: 175.8 (C-1, lactone), 159.6 (—C=N—), 104.3 (C-1'), 99.3 (C-1''), 51.1 (C-8-CH$_2$), 40.3 [C-3'-N(CH$_3$)$_2$]

MIC (mcg/mL) (clinical isolates) Strept. pneumoniae 0.5; Strept. serol. group A 0.5

EXAMPLE 2

ANHYDRO OLEANDOMYCIN OXIME Ib

Anhydro oleandomycin (IIb) (2.2 g, 0.0033 mole) was dissolved in dry pyridine (4 mL), $NH_2OH.HCl$ (1.2 g, 0.017 mole) was added and the reaction mixture was stirred at room temperature in nitrogen stream for 18 hours. Pyridine was removed by evaporation under reduced pressure and by addition of water. To the water suspension chloroform was added, the pH was adjusted to 8.3 by the addition of NaOH (20% solution in water) and it was extracted with chloroform (3×35 ml). The extract was dried ($K_2CO_3$) and evaporated to dryness, yielding 2.1 g (93.0%) of a white solid.

$R_f$
(A) 0.52
(B) 0.37

M+ 684

1H-NMR (DMSO-d6) δ, ppm: 2.21 [6H, s, (CH3)2N—], 3.34 (3H, s, 3″—OCH3), 10.97 (1H, s, =NOH), disappears by exchange with D2O 13C-NMR (CDCl3) δ, ppm: 174.8 (C-1, lactone), 157.3 (—C=N—), 104.6 (C-1′), 99.5 (C-1″), 130.1 (C-11), 135.0 (C-10), 51.2 (C-8-CH2), 40.3 [C-3′-N(CH3)2]

MIC (mcg/mL) (clinical isolates) Strept. pneumoniae 2.0; Strept. serol. group A 1.0

EXAMPLE 3

8-METHYLENE-OLEANDOMYCIN OXIME Ic 8-methylene-oleandomycin (IIc) (2.7 g, 0.004 mole) was dissolved in dry pyridine (19 mL) and hydroxylamine hydrochloride (1.35 g, 0.019 mole) was added. The reaction mixture was stirred at room temperature in nitrogen stream for 2 hours. After extraction with dichloromethane at pH 5 and 7, the product was isolated by the evaporation of the extract to dryness at pH 7 (2.0 g; 73.0%).

$R_f$
(A) 0.58
(B) 0.35
M+ 686

1H-NMR (DMSO-d6) δ, ppm: 2.29 [6H, s, (CH3)2N—], 3.34 (3H, s, 3″—OCH3), 10.28 (1H, s, =NOH), disappears by exchange with D2O 13C-NMR (CDCl3) δ, ppm: 176.6 (C-1, lactone), 163.4 (—C=N—), 141.4 (C-8), 116.4 (C-8a), 104.6 (C-1′), 99.2 (C-1″), 40.4 [C-3′—N(CH3)2]

MIC (mcg/mL) (clinical isolates) Strept. pneumoniae 1.0; Strept. serol. group A 1.0

EXAMPLE 4

8-METHYL-OLEANDOMYCIN OXIMES Id AND Ie 8-methyl-oleandomycin (a mixture of anomers IId and IIe) (1.2 g, 0.0018 mole) was dissolved in dry pyridine (4 mL) and NH2OH.HCl (0.6 g, 0.0086 mole) was added and it was stirred at room temperature in nitrogen stream for 2 hours. Thin layer chromatography showed a complete conversion of the compound IId ($R_f/A/=0.67$) after 5 hours into the product Id ($R_f/A/=0.48$), while the starting compound IIe ($R_f/A/=0.63$) afforded the product Ie ($R_f/A/=0.57$) after 40 hours. By means of gradient extraction with methylene chloride at pH 7.5, there was obtained the product as a mixture of isomers (0.7 g, 57%), which could be separated on a column of silicagel with (CH2Cl2/CH3OH 85:15).

The isomers had the following physico-chemical characteristics:

Id
$R_f$
(A) 0.48
(B) 0.34
M+ 688

1H-NMR (DMSO-d6) δ, ppm: 2.42 [6H, s, (CH3)2N—], 3.43 (3H, s, 3″—OCH3), 10.40 (1H, s, =NOH), disappears by exchange with D2O 13C-NMR (CDCl3) δ, ppm: 176.8 (C-1, lactone), 165.5 (—C=N—), 104.7 (C-1′), 99.5 (C-1″), 40.4 [C-3′—N(CH3)2]

Ie
$R_f$(A) 0.57
M+ 688

1H-NMR (DMSO-d6) δ, ppm: 2.29 [6H,s,(CH3)2N—], 3.32 (3H,s,3″—OCH3), 10.61 (1H,s,=NOH), disappears by exchange with D2O 13C-NMR (CDCl3) δ, ppm: 176.2 (C-1, lactone), 168.6 (—C=N—), 104.2 (C-1′), 98.5 (C-1″), 40.4 [C-3′-N(CH3)2]

Activity: 657 u/mg Sarcina lutea ATCC 9341

We claim:

1. Oleandomycin oxime of the formula I

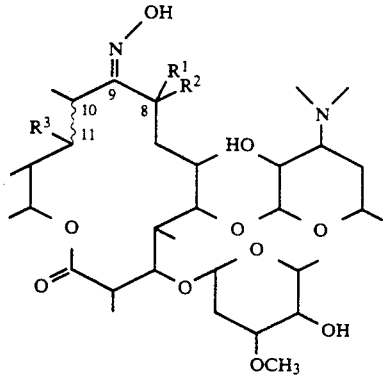

wherein $R^1$ stands for hydrogen or —CH3, $R^2$ stands for —CH3 or hydrogen or $R^1$ and $R^2$ stand together for an epoxide group or for =CH2, $R^3$ stands for —OH, whereas the ~ line stands for a single or a double bond.

2. A compound of the formula I according to claim 1, wherein $R^1$ and $R^2$ stand together for an epoxide group, $R^3$ stands for —OH group and the ~ line stands for a single bond.

3. A compound of the formula I according to claim 1, wherein $R^1$ and $R^2$ stand together for an epoxide group and the ~ line stands for a double bond.

4. A compound of the formula I according to claim 1, wherein $R^1$ and $R^2$ stand together for =CH2 group, $R^3$ stands for —OH group and the ~ line stands for a single bond.

5. A compound of the formula I according to claim 1, wherein one of $R^1$ or $R^2$ stands for hydrogen, and the other one of $R^1$ or $R^2$ stands for —CH3 group, $R^3$ stands for —OH group and the ~ line stands for a single bond.

* * * * *